United States Patent
Kadavy et al.

(10) Patent No.: US 12,053,310 B2
(45) Date of Patent: Aug. 6, 2024

(54) MACHINE VISION NEEDLE COUNTING IMAGING TRAY

(71) Applicant: The Cleveland Clinic Foundation, Cleveland, OH (US)

(72) Inventors: Thomas Kadavy, Bellevue, WA (US); Cristiano Quintini, Beachwood, OH (US); Douglas R. Johnston, Shaker Heights, OH (US); Edward G. Soltesz, Westlake, OH (US); Jose Romero, Avon, OH (US); William Kolosi, Stow, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 17/734,434

(22) Filed: May 2, 2022

(65) Prior Publication Data
US 2022/0346904 A1 Nov. 3, 2022

Related U.S. Application Data

(60) Provisional application No. 63/183,200, filed on May 3, 2021.

(51) Int. Cl.
| | |
|---|---|
| *A61B 50/33* | (2016.01) |
| *A61B 50/30* | (2016.01) |
| *F21V 8/00* | (2006.01) |
| *G02B 27/30* | (2006.01) |
| *G06V 10/145* | (2022.01) |
| *G06V 20/00* | (2022.01) |
| *H04N 23/56* | (2023.01) |

(52) U.S. Cl.
CPC .......... *A61B 50/33* (2016.02); *A61B 50/3001* (2016.02); *G02B 6/0006* (2013.01); *G02B 6/001* (2013.01); *G02B 27/30* (2013.01); *G06V 10/145* (2022.01); *G06V 20/00* (2022.01); *H04N 23/56* (2023.01); *G06V 2201/034* (2022.01)

(58) Field of Classification Search
CPC .. A61B 50/33; A61B 50/3001; G06V 10/145; G06V 20/00; G06V 2201/034; H04N 23/56; G02B 6/0006; G02B 6/001; G02B 27/30
See application file for complete search history.

(56) References Cited

U.S. PATENT DOCUMENTS

| | | | | |
|---|---|---|---|---|
| 5,355,289 A | * | 10/1994 | Krenn | ................. F21V 33/0036 362/249.14 |
| 10,807,767 B1 | * | 10/2020 | Kriesel | ...................... C09J 4/00 |

(Continued)

FOREIGN PATENT DOCUMENTS

| | | |
|---|---|---|
| DE | 202011050001 U1 | 7/2011 |
| WO | 2014167252 A1 | 10/2014 |

OTHER PUBLICATIONS

International Search Report & Written Opinion issued in corresponding PCT application No. PCT/US2022/027268 dated Aug. 12, 2022, 16 pages.

*Primary Examiner* — James T Boylan
(74) *Attorney, Agent, or Firm* — Tucker Ellis LLP

(57) ABSTRACT

A needle collection and counting tray for use in a clinical setting, such as an operating room, into which a user deposits used needles. The tray is then placed into a counting and identification machine the utilizes object recognition technology to identify and count the needles on the tray.

30 Claims, 12 Drawing Sheets

(56) References Cited

U.S. PATENT DOCUMENTS

| | | | | |
|---|---|---|---|---|
| 2008/0278460 A1* | 11/2008 | Arnett | ............ | G06F 3/0428 |
| | | | | 362/555 |
| 2013/0314943 A1* | 11/2013 | Huang | ............ | G02B 6/0053 |
| | | | | 362/606 |
| 2014/0291397 A1* | 10/2014 | Caputo | ............ | G16H 15/00 |
| | | | | 235/385 |
| 2015/0366617 A1* | 12/2015 | Frushour | ............ | A61B 50/26 |
| | | | | 206/363 |
| 2017/0074486 A1* | 3/2017 | Flynn | ............ | F21V 5/02 |
| 2017/0192160 A1* | 7/2017 | Ham | ............ | G02B 6/0055 |
| 2019/0362839 A1* | 11/2019 | Quintini | ............ | G16H 30/20 |
| 2020/0013191 A1* | 1/2020 | Berning | ............ | A61B 50/24 |
| 2021/0231856 A1* | 7/2021 | Tang | ............ | G02B 6/002 |
| 2022/0277441 A1* | 9/2022 | Schlaudraff | ............ | G06F 17/15 |

\* cited by examiner

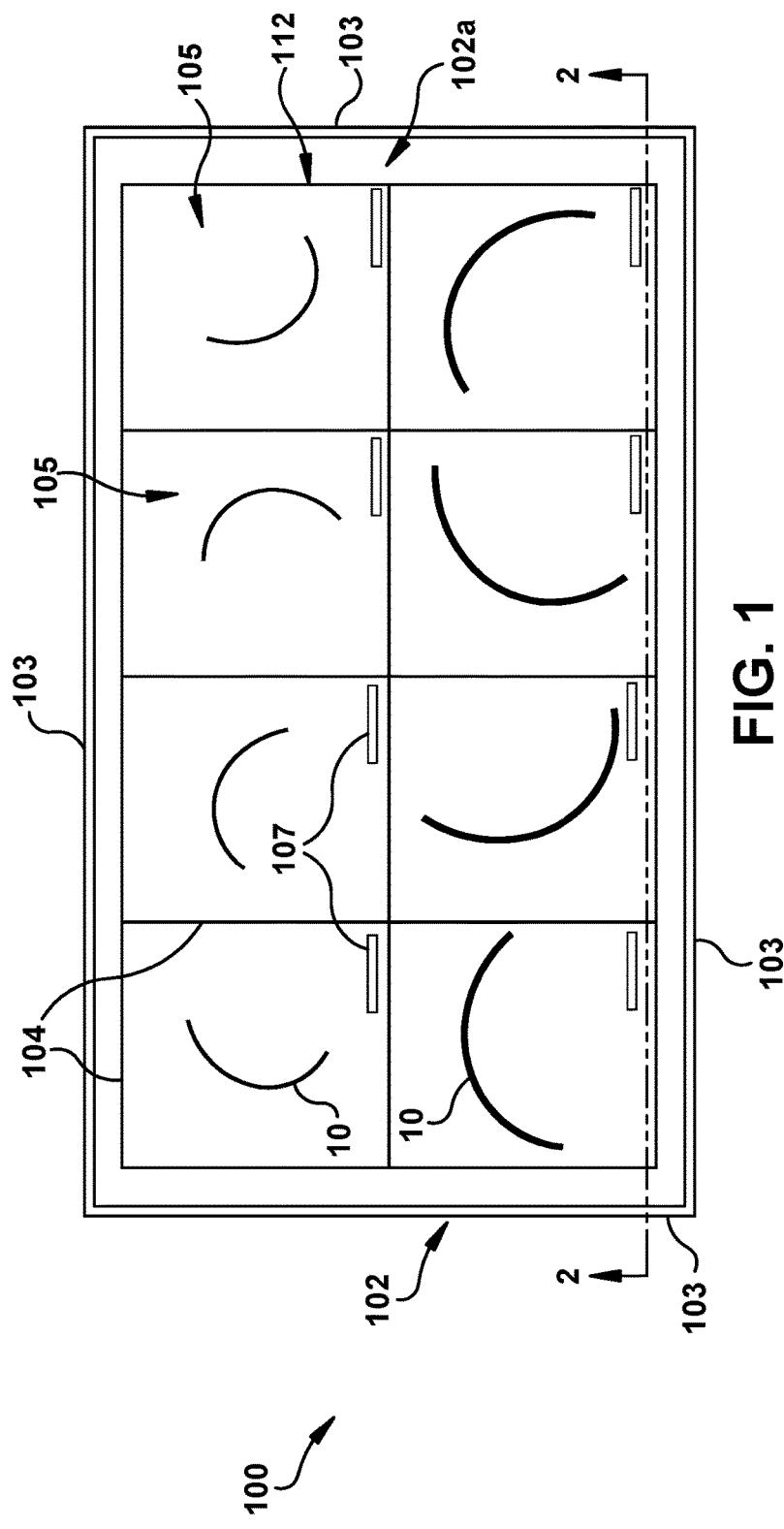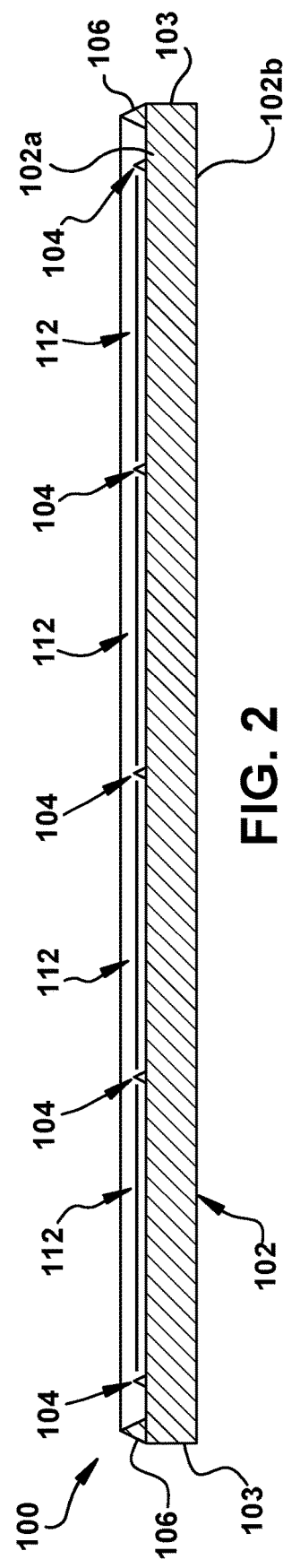

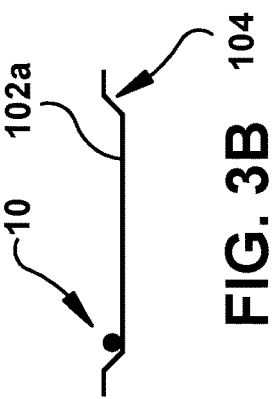
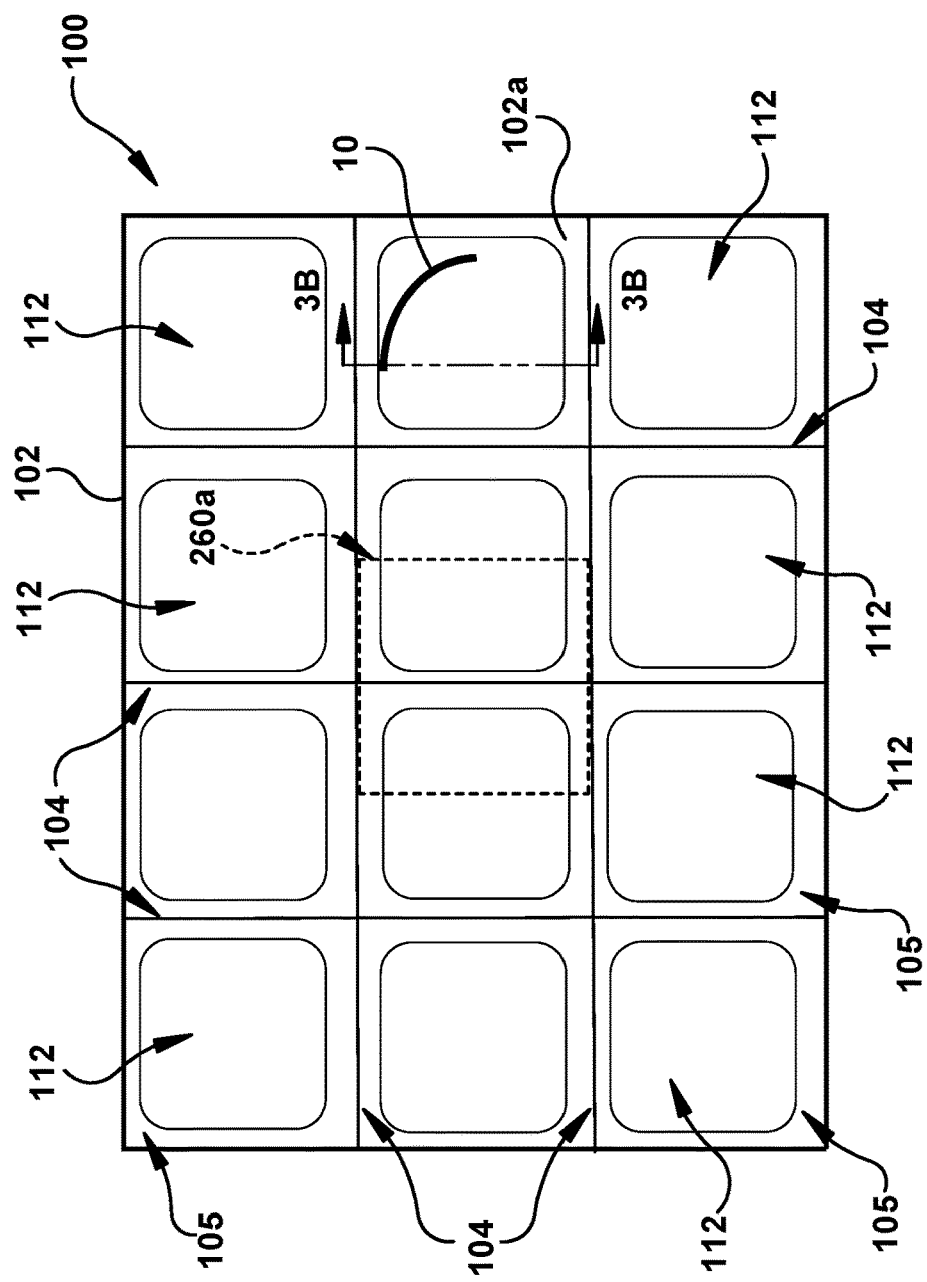

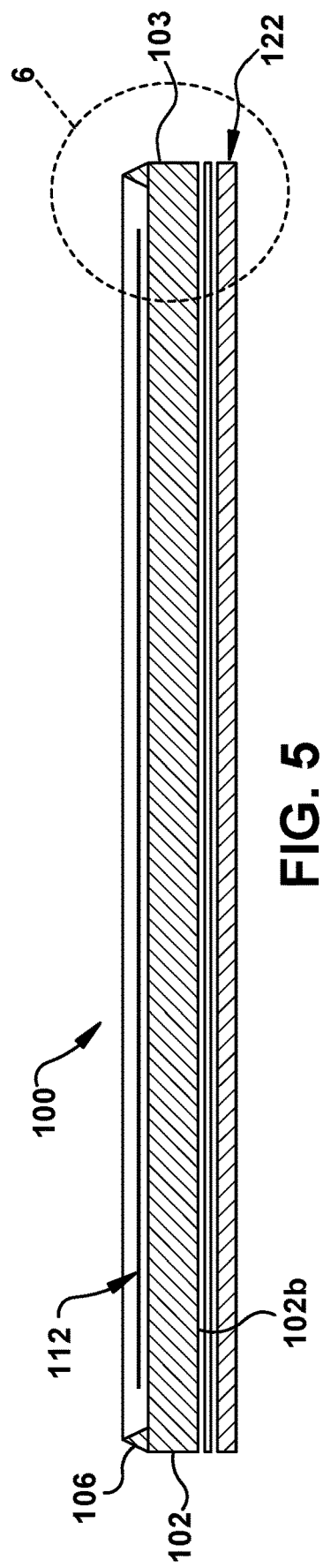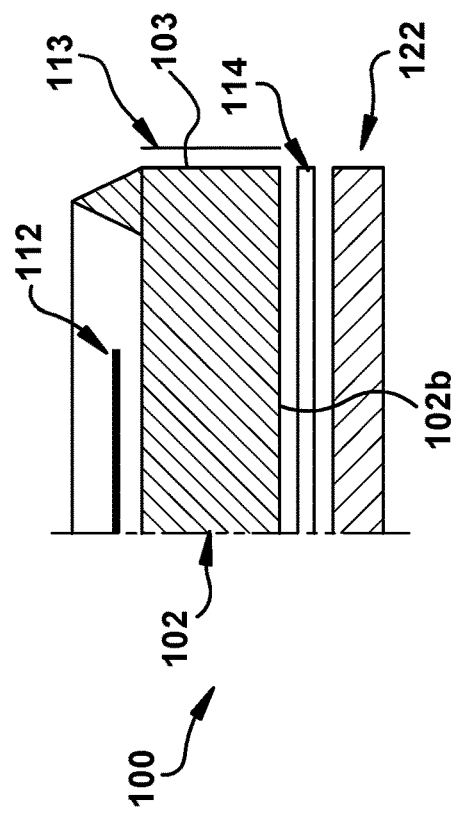

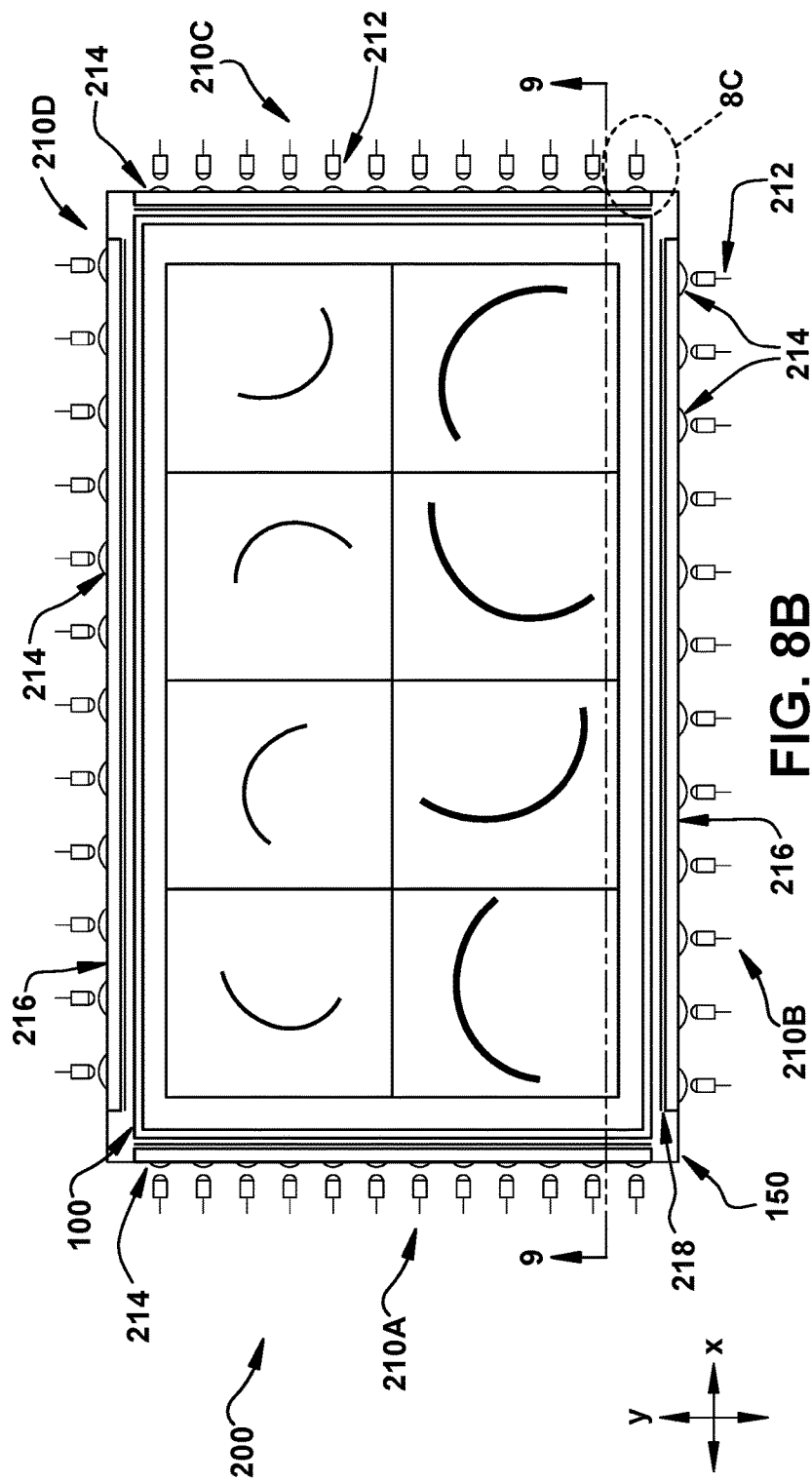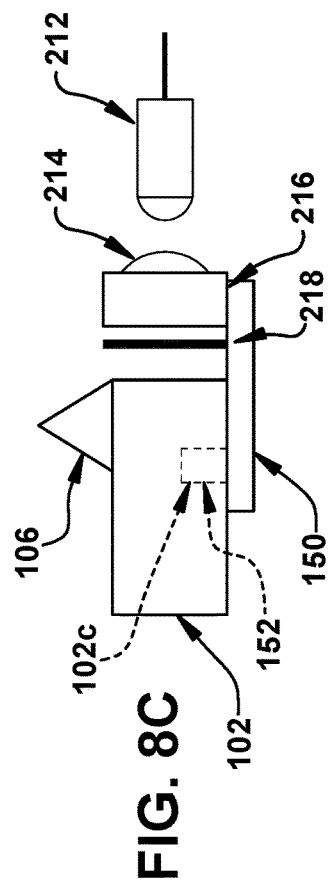
FIG. 8B
FIG. 8C

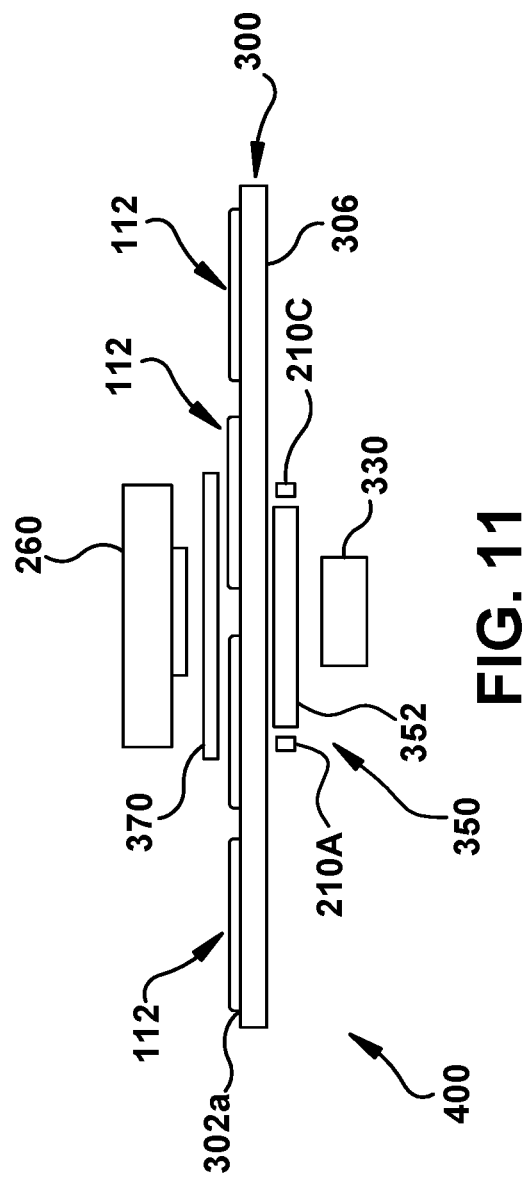

MACHINE VISION NEEDLE COUNTING IMAGING TRAY

CROSS-REFERENCE TO RELATED APPLICATIONS

This application claims priority to U.S. Provisional Patent Application No. 63/183,200 filed on May 3, 2021, the entirety of which is incorporated herein by reference.

FIELD OF THE INVENTION

The present invention relates to a needle collection and counting tray for use in a clinical setting, and more particularly, to a needle collection and counting tray that can be used in an operating room for collecting and counting needles used during an operating procedure.

BACKGROUND OF INVENTION

Needles and other small surgical implements are used extensively during operating procedures. It is critical that before the patient is released from the operating room, the operating personnel account for each needle used during the operating procedure. If a needle cannot be located, then the patient must remain in the operating room, with the surgical site open, and additional equipment, e.g., x-ray machines must be brought into the operating room to determine if and where a needle may still reside within the patient. A lost needle can result in long delays and take the operating room out of use for extended periods of time.

It is desirable to have an apparatus that operating personnel can use to collect and count needles or other small implements at the end of an operating procedure.

SUMMARY OF INVENTION

There is provided a surgical implement collecting tray that includes an optically transmissive body having a lower surface, an upper surface, and one or more edges disposed about a periphery of the body. At least one of the lower surface and the one or more edges is configured to receive light from an adjacent light source, wherein the body is configured to emit at least a portion of the received light through the upper surface. A plurality of defined receiving areas are defined on or adjacent to the upper surface and are configured to receive respective surgical implements therein, wherein the tray is configured to direct light exiting the upper surface thereof in a collimated direction away from the upper surface.

There is provided a collimating film on the upper surface of the optically transmissive body effective to direct the light exiting the upper surface in the collimated direction.

There is provided a reflective layer at the lower surface of the optically transmissive body that is adapted to redirect light incident thereon toward the upper surface.

There is provided a reflective layer at the one or more edges for directing light incident thereon into the body.

There is provided an optically transmissive adhesive applied to an upper surface of the collimating film onto which a surgical implement may be placed and securely held within one receiving area.

There is provided a lip disposed about a periphery of the upper surface of the body for re-directing light toward the body.

It is provided that the receiving areas are defined by gridlines formed as embossments in the upper surface of the optically transmissive body.

It is provided that the embossments include prismatic embossments standing proud of the upper surface of the optically transmissive body and being configured to redirect light incident thereon back into the body.

It is provided that the receiving areas are defined by graphics printed on the upper surface of the optically transmissive body that are transmissive to light of a predetermined wavelength.

There is provided a magnetic sheet disposed beneath the reflective layer and adapted to attract ferromagnetic surgical implements disposed in the receiving areas of the tray via magnetic interaction therewith through the optically transmissive body and the reflective layer.

There is provided a surgical implement deposited into at least one receiving area of the tray.

It is provided that the surgical implement is a needle.

There is provided a surgical-implement counting system that includes a collection tray according to the foregoing embodiment and an edge light assembly configured to illuminate an adjacent one of the one or more edges of the optically transmissive body of the collection tray.

In the system, the edge light assembly includes a plurality of light collecting lenses associated or configured to be aligned with respective light emitting diodes. The light collecting lenses all are coupled to a light pipe that extends along the adjacent edge of the optically transmissive body and is configured to receive light emitted by the light emitting diodes. An exit diffuser also extends along the adjacent edge of the optically transmissive body and is configured to direct light from the light pipe to the adjacent edge of the optically transmissive body.

There is further provided a system for identifying and counting surgical implements. The system includes a counting machine having a station configured to receive therein a tray having surgical implements disposed thereon. A lighting assembly is adapted to direct light toward a tray when received in the station. A sensor is mounted above the station and is adapted to detect silhouetted images of surgical implements disposed on the tray when received in the station from the light directed thereto from the lighting assembly. A processor is adapted to determine a size and number of surgical implements from the silhouetted images, thereby recognizing particular surgical implements.

It is provided that the processor is further adapted to count a plurality of the thusly recognized particular surgical implements during or appurtenant to an operating procedure.

It is provided that the tray includes an optically transmissive body having a lower surface, an upper surface, and one or more edges disposed about a periphery of the body. At least one of the lower surface and the one or more edges is configured to receive light from the lighting assembly disposed adjacent thereto, wherein the body is configured to emit at least a portion of the received light through the upper surface. The tray is configured to direct light exiting the upper surface of the optically transmissive body in a collimated direction away from the upper surface toward the sensor.

There is provided a reflective layer at the lower surface of the tray for directing light incident thereon toward the upper surface of the tray.

It is provided that the lighting assembly includes a plurality of light collecting lenses associated or configured to be aligned with respective light emitting diodes. The light collecting lenses all being coupled to a light pipe that extends along an adjacent edge of the tray when received in the station and being configured to receive light emitted by the light emitting diodes. An exit diffuser extends along the adjacent edge of the tray when received in the station and is configured to direct light from the light pipe to the adjacent edge of the tray when received in the station.

It is provided that the lighting assembly includes a backlight assembly disposed beneath the station for receiving the tray and configured to direct light upward through the station and into and through a lower surface of the tray. The backlight assembly includes a plurality of light collecting lenses aligned with respective light emitting diodes. The light collecting lenses are all coupled to a light pipe that extends along an adjacent edge of an internally optically reflective body. The optically reflective body is configured to direct light received from the light pipe toward the lower surface of the tray when the tray is received in the station.

There is provided an actuator adapted to move the tray when received in the station in a plane parallel to an upper surface of the tray.

There is provided an actuator adapted to move the sensor in a plane parallel to an upper surface of the tray.

It is provided that the lighting assembly is disposed above the station to illuminate an upper surface of the tray when received in the station.

It is provided that the tray is received in the station and an absorbing element is positioned on or applied to the upper surface of the tray. The absorbing element being adapted to absorb the light from the lighting assembly.

BRIEF DESCRIPTION OF THE DRAWINGS

FIG. 1 is top view of a collection and counting tray having a plurality of needles disposed thereon;

FIG. 2 is a cross-sectional view of the collection and counting tray of FIG. 1 taken along line 2-2 in FIG. 1;

FIG. 3A is a top view of the collection and counting tray of FIG. 1 having gridlines according to a second embodiment;

FIG. 3B is a cross-sectional view of the collection and counting tray of FIG. 3A taken along line 3B-3B in FIG. 3A;

FIG. 5 is a cross-sectional view as in FIG. 2, illustrating a reflective coating/film and a disposable magnet sheet attached to a lower surface of the tray;

FIG. 6 is an enlarged view of an edge of the collection and counting tray as indicated at 6 in FIG. 5;

FIG. 8B is a top view of the collection and counting tray of FIG. 1 positioned on a frame adjacent light emitting diodes (LEDs) of the automated counting and identification machine of FIG. 8A;

FIG. 8C is an enlarged side view of the edge of the tray, frame and LEDs indicated at 8C in FIG. 8B;

FIG. 11 is a side schematic view of a collection and counting tray according to a second embodiment positioned in an automated counting and identification machine according to the second embodiment;

DETAILED DESCRIPTION OF PREFERRED EMBODIMENT

Figure 8A:
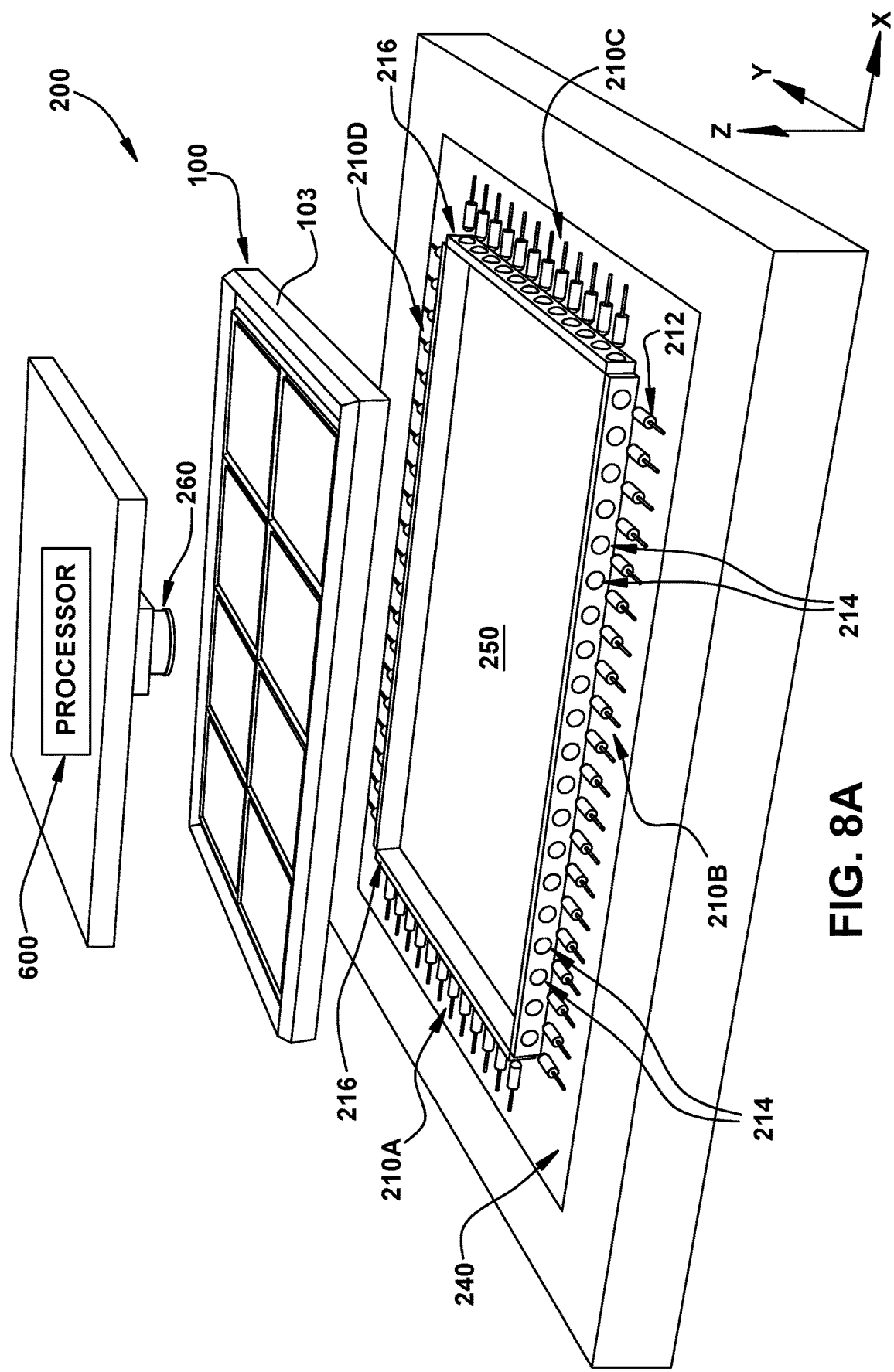
FIG. 8A is an exploded perspective schematic view of the collection and counting tray of FIG. 1 and an automated counting and identification machine.

Referring to the drawings, FIGS. 1 and 2 show a collection and counting tray 100 (hereinafter referred to as "tray 100") for use in an automated counting and identification machine 200 (e.g. as seen in FIG. 8A).

The tray 100 includes a body 102 that is made from an optically transmissive plastic, for example but not limited to acrylic. The body 102 is a generally planar (e.g. rectangular-shaped) element and is dimensioned to receive needles 10 or other surgical implements. on an upper surface 102a thereof. In FIG. 1, the body 102 is illustrated as receiving eight needles 10 but it is contemplated that the body 102 can be dimensioned to receive any number of needles 10. A plurality of grid lines 104 are formed on the upper surface 102a. The grid lines 104 define fixed receiving areas 105 on the upper surface 102a that each are dimensioned to receive one or more needles 10. It is contemplated that the grid lines 104 may take the form of prismatic embossments (see, FIG. 2) that stand proud of the upper surface 102a. The prismatic embossments may be referred to as "anti-loss" features that are configured to redirect light in a desired direction, e.g. back into the body 102 of the tray 100 so that that light may be reflected out the upper surface 102a. The tray 100 is illustrated as having eight square-shaped receiving areas 105 but it is contemplated that the tray 100 could include more or fewer receiving areas 105 and the receiving areas 105 may have a shape other than square.

According to another embodiment, illustrated in FIGS. 3A and 3B, the grid lines 104 take the form of elongated, angled ridges (see, FIG. 3B) on the upper surface 102a that are formed at the edges of the receiving areas 105. The angled ridges are raised above the upper surface 102a and define boundaries against which the needles 10 may rest. The angled ridges may be placed adjacent the boundaries of the receiving areas 105 to urge the needles 10 toward a center of the respective receiving area 105. When printed grid lines are used (discussed below), the angled ridges may hinder the needles 10 from resting on the grid lines. The angled ridges may hinder significant overlap of the needle 10 with the grid lines, thereby improving the ability of the automated counting and identification machine 200 to detect and/or count the needles 10.

Figure 4A:
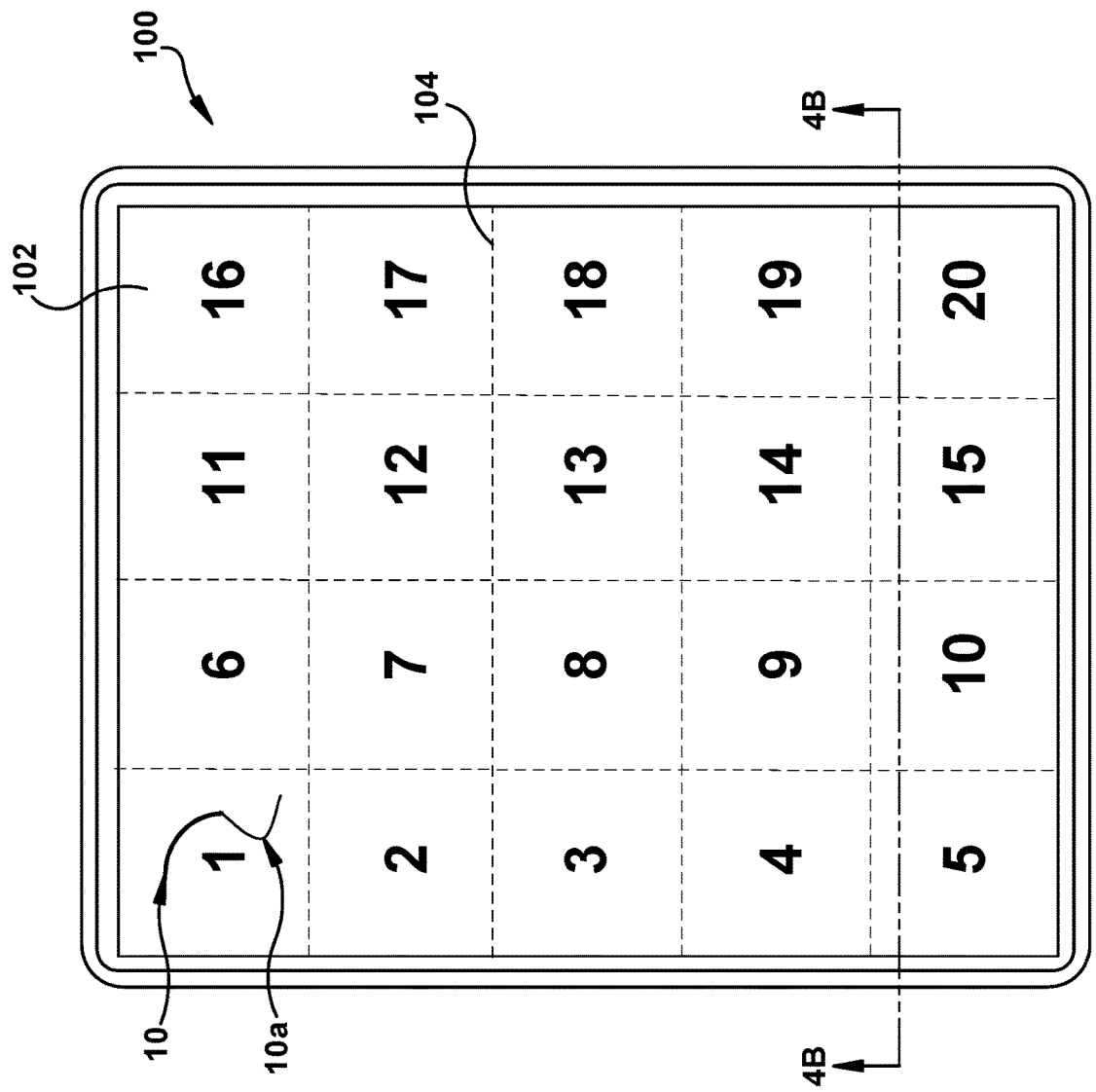
FIG. 4A is a top view of the collection and counting tray of FIG. 1 having gridlines according to a third embodiment.
Figure 4B:
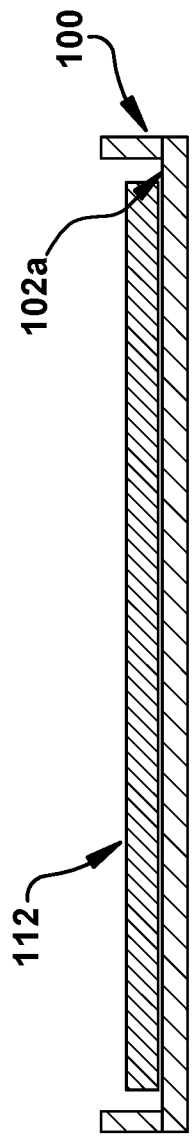
FIG. 4B is a cross-sectional view of the collection and counting tray of FIG. 4A taken along line 4B-4B of FIG. 4A.

According to another embodiment, illustrated in FIGS. 4A and 4B, the grid lines 104 take the form of printed graphics, e.g. printed lines on an upper surface 102a of the body 102. Numerals also may be printed on the surface 102a to sequentially number and identify individual receiving areas 105. The graphics are printed with an ink that is human readable but transmissive to the light of a predetermined wavelength. As described in detail below, the graphics do not influence the ability of the count and capture machine 200 to detect the needles 10 on the tray 100. The graphics may be selected to aid the user in placing the needles 10 at the correct locations on the tray 100 and in counting the number of needles 10 on the tray 100.

Referring back to FIG. 1, it is also contemplated that the one or more of the receiving areas 105 may include an optical calibration feature 107 that may be used to calibrate an automated counting and identification machine 200, as described in detail below. In one embodiment, the calibration features 107 are rectangular features of predetermined size and position. These features can be printed on or embossed in the upper surface 102*a* of the body 102, and they can be of any desired size and shape. The calibration features 107 are essentially landmarks that are recognized by a camera or other sensor (described below) that allow for correlating the objects such as needles 10 that are received on the tray with their respective locations on that tray; e.g. to correlate a particular needle 10 with the associated receiving area 105.

Referring to FIG. 2, the body 102 is configured to disperse light incident on the tray using internal reflection. In particular, the body 102 is configured such that light incident on edges 103 of the body 102 is internally reflected to exit through the upper surface 102*a* of the body 102.

A lip 106 is positioned on the upper surface 102*a* about an outer periphery of the upper surface 102*a*. The lip 106 is configured to redirect light back toward a center of the body 102 to aid in recognizing needles 10 disposed on the upper surface 102*a*, as described in detail below. The lip 106 is referred to as an "anti-loss lip" and takes the form of an elongated prism (e.g. an elongated triangular prism as shown) disposed on or formed with the upper surface 102*a* to redirect light in a desired direction.

A collimated film 112 is positioned on the upper surface 102*a* of the tray 100 in each receiving area 105. The collimated film 112 is configured to direct light that has passed through the tray 100 in a predetermined direction, as described in detail below. During use, the needles 10 are placed on the collimated film 112 resting on the upper surface 102*a* of the tray 100. In the embodiment illustrated in FIG. 4B wherein the grid lines are printed on the upper surface 102*a* of the body 102, the collimated film 112 may be a single piece the covers the entire upper surface 102*a* of the body 102.

It is contemplated that the collimated film 112 may include an adhesive, e.g. a layer or coating of pressure-sensitive adhesive (PSA) on its upper surface (not shown) to help secure the needles 10 to the collimated film 112 when placed thereon based on the tackiness of the adhesive. If used, the adhesive would be optically transmissive so as to minimally impact the light transmitted through the film 112 on exiting the upper surface of the tray 100.

Referring to FIGS. 5 and 6, a reflective (preferably opaque) layer 114, e.g. a coating or a film, is positioned on or adjacent to a lower surface 102*b* of the body 102. The coating or film 114 is configured so that light incident at the lower surface 102*b* cannot pass through and exit via the lower surface 102*b*. Rather, any such light that reaches the lower surface 102*b* (and thus the reflective film 114) through internal reflection within the body 102 will be directed or reflected back upward toward the upper surface 102*a* of the tray 100, from which the light will exit.

A disposable magnet sheet 122 may be attached to a lower surface of the film 114. The disposable magnet sheet 122 can attract ferromagnetic needles 10 or other implements to the upper surface 102*a* of the tray 100 when placed thereon, via a magnetic field propagating through the tray 100 and the intervening film 114. Using either or both the aforementioned adhesive and/or magnet sheet 122, needles 10 or other surgical implements may be held within the receiving areas 105 on the tray 100 during both use and transport. The magnet sheet 122 will be useful for this purpose only if the needles 10 or other implements to be held are made of or comprise sufficient ferromagnetic material to be held in place via magnetic forces.

Figure 7:
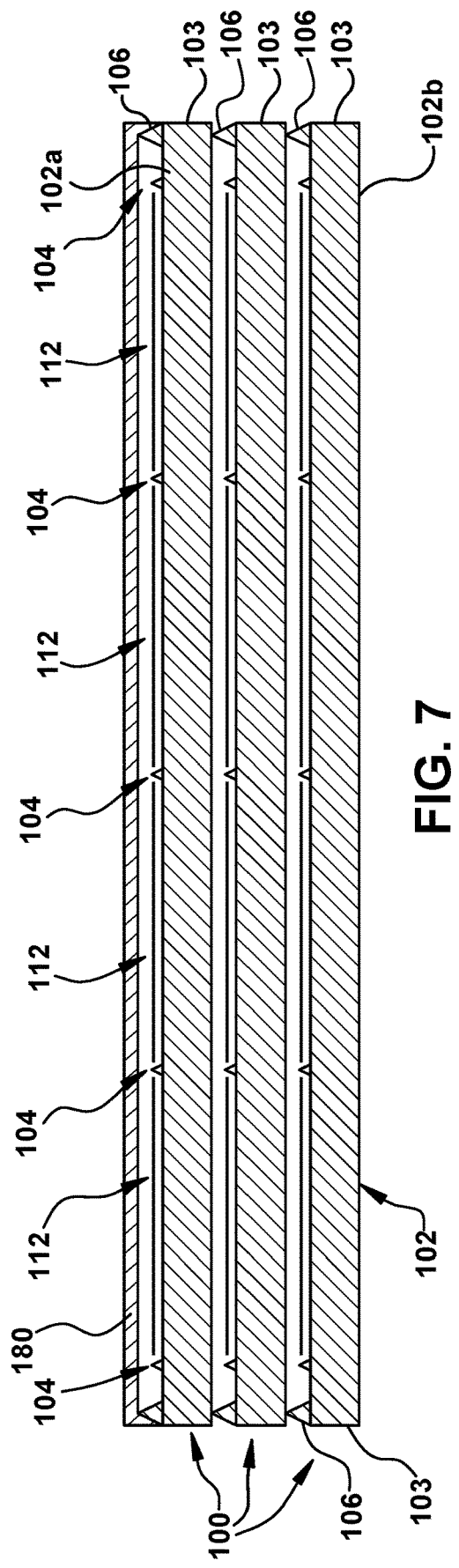
FIG. 7 is a side view of a plurality of collection and counting trays of FIG. 1, in a stacked arrangement.

Referring to FIG. 7, it is contemplated that trays 100 may be configured so that they may be stacked on top of each other. When stacked, each tray 100 is configured to cover and/or capture the needles 10 in the tray 100 below it. A cover 180 may be provided for enclosing the needles 10 on a respective tray 100 or on the uppermost tray 100 in a stack of trays.

Referring to FIGS. 8A-8C, a tray 100 is shown positioned in an automated counting and identification machine 200 for detecting needles in the receiving areas of the tray. In general, the machine 200 has a lighting assembly that includes edge light assemblies 210A-210D and light emitting diodes (LEDs) 212. In the illustrated embodiment, four edge light assemblies 210A-210D are positioned adjacent to respective edges 103 of the tray 100. The edge light assemblies 210A-210D can be integrated into the machine 200 such that the tray 100 is simply placed therein for needle detection. Alternatively, as explained below the edge light assemblies 210A-210D can be disposed in or as part of a frame that is fitted to each tray 100 wherein the combined frame-and-tray then is disposed in the machine for needle detection. Either way, in operation each edge light assembly 210A-210D extends adjacent to a plurality of light emitting diodes (LEDs) 212 distributed along a length of the respective edge 103 of the tray 100, each being associated with and positioned adjacent to a respective light collecting lens 214 of the edge light assembly 210A-210D. The light collecting lenses 214 along each edge 103 of the tray 100 are positioned on a light pipe 216 of the edge light assembly 210A-210D. Each light pipe 216 directs the light collected from the associated LEDs 212, via associated lenses 214, to an exit diffuser 218 of the edge light assembly 210A-210D running along the respective edge 103 and disposed between that edge 103 and the light pipe 216. Light leaving the exit diffuser 218 is then incident on the adjacent edge 103 of the tray 100.

It is contemplated that there may include fewer than four edge light assemblies 210A-210D, and that edge(s) 103 of the tray 100 not positioned adjacent to an edge light assembly may have a reflective coating 113 (FIG. 6) thereon. The reflective coating 113 may be selected so that light incident on these edges 103 via internal reflection within the body 102 of the tray 100 is reflected back into the tray 100 instead of being emitted to the surrounding environment.

During an operating procedure, the tray 100 may be placed near surgical personnel to allow for easy collecting of needles 10 used during the procedure. Referring to FIGS. 8B and 8C, once each receiving area 105 on a particular tray 100 is filled or the operating procedure is complete, that tray 100 may be placed into a frame 150 having the edge light assemblies 210A-210D. The frame 150 may include pegs 152 that are positioned and dimensioned to engage mating recesses 102*c* in the body 102 of the tray 100. The combination of the frame 150 and the tray 100 may then be placed into the machine 200 as noted above so that the LEDs 212 (which may be resident in the machine) are aligned with the respective edge light assemblies 210A-210D adjacent to respective edges 103 of the tray body 102. Alternatively, positioning the tray 100 in the machine 200 may include placing the tray 100 without the frame 150 noted above, wherein the edge light assemblies 210A-210D are disposed instead in or as part of the machine 200 itself (see, FIG. 8A). In this embodiment, the edge light assemblies 210A-210D may define a station 250 that is sized to receive the tray 100, such that they will be positioned adjacent to respective edges 103 of the tray 100 to illuminate it for needle-recognition and counting on placement of the tray.

Once the tray 100 is positioned with edge light assemblies 210A-210D disposed adjacent respective edges 103 thereof (e.g. in the machine 200), the LEDs 212 are energized. Light from the LEDs 212 is directed into the adjacent edges 103 of the tray 100. The tray 100 acts as a light guide to disperse the light from the LEDs 212 throughout the tray 100 using internal reflection. Internally transmitted and reflected light is directed out the upper surface 102a of the tray. Light that may be incident on the lower surface 102b of the tray 100 (e.g. via internal reflection in the tray 100) is reflected upward toward the upper surface 102a by the reflective coating or film 114.

Light that exits through the upper surface 102a is collimated or aligned by the collimating film 112 in a direction that preferably is perpendicular to the upper surface 102a. In this respect, the light passing by the needles 10 creates silhouettes with crisp edges that may be recognized by an imaging camera 260 (FIG. 8A) of the machine 200, whose optical axis preferably is aligned with the direction of collimated light exiting the film 112. In essence, the tray 100 becomes a backlight that enables silhouette imaging of the needles 10. The crisp edges of the needles 10 that can be visualized from their silhouettes via collimated light help to improve accuracy in detecting not only the presence of needles 10 on the tray 100, but which specific needles (and how many of each) are present on the tray 100. This information then can be compared to the number of each specific needle type known to have been used during the procedure.

It is contemplated that the LEDs 212 may emit light of a single wavelength. The collimating film 112 may be configured so that it is some percentage (e.g. >90%) transmissive to the selected single wavelength. The collimated film 112 may be selected to be opaque or substantially opaque to other wavelengths so that these other wavelengths are not transmitted to the camera 260 of the machine 200. The ability of the machine 200 to detect or recognize accurately the needles 10 on the tray 100 can be improved by limiting the transmission of light of these other wavelengths to the camera 260, so that substantially light of only the single wavelength reaches the camera 260 for silhouette visualization and detection.

It is contemplated that the predetermined wavelength of the light may be selected such that a suture thread 10a (FIG. 4A) attached to the needle 10 is transmissive to the light. For example, infrared (IR) light may pass through the suture thread 10a but be reflected by the needle 10. As a result, IR light transmitted through the suture thread 10a will not materially impact the silhouette of the needle detected by the camera 260, which then will be able to make an accurate identification despite the needle 10 retaining a suture-thread tail.

It is also contemplated that the tray 100 may be tinted or colored to transmit only light of the selected single wavelength; or at least to reduce transmission of light of other wavelengths. This further reduces the likelihood that (or the magnitude at which) light of other wavelengths will be transmitted to the camera 260 to negatively impact the ability of the machine 200 to detect or recognize accurately the needles 10 on the tray 100.

Figure 9:
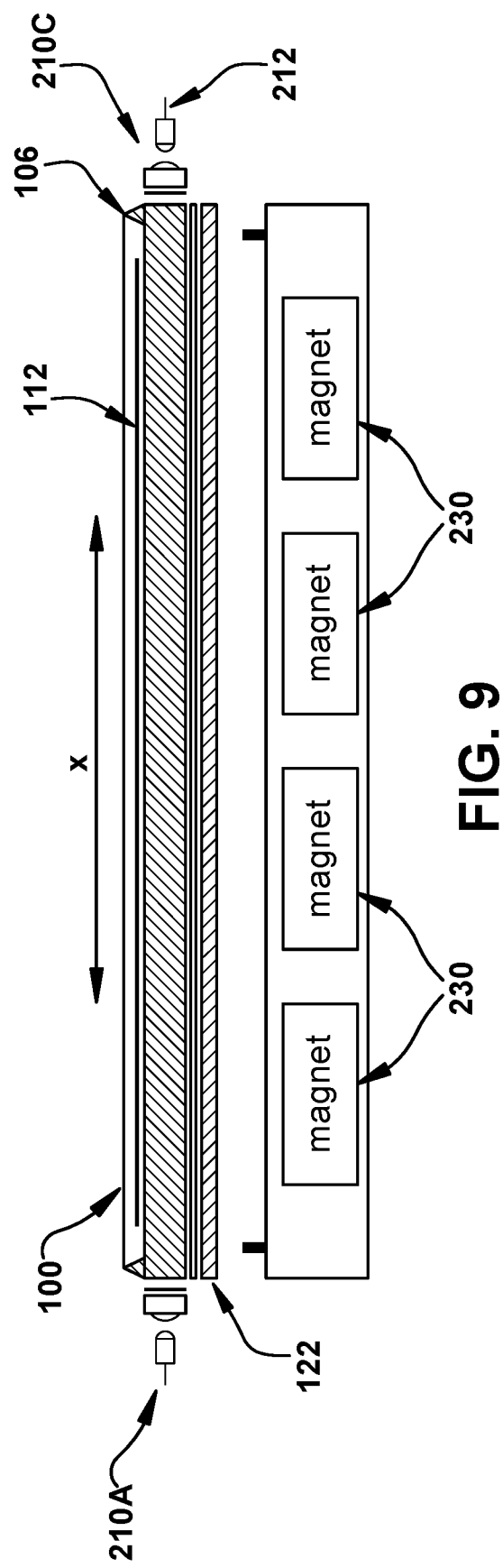
FIG. 9 is a cross-section of the collection and counting tray positioned in the automated counting and identification machine of FIG. 8B taken along line 9-9 of FIG. 8B.

Referring to FIG. 9, as described above, the tray 100 can include the disposable magnetic sheet 122 effective to hold ferromagnetic needles 10 on the tray 100. Alternatively, or in combination with the magnetic sheet 122, the machine 200 may include a plurality of high strength magnet assemblies 230. Once the tray 100 is placed in the machine 200 during or after an operating procedure, the magnet assemblies 230 may be used to retain ferromagnetic needles 10 on the tray 100 to ensure they remain fixed in place during silhouette visualization and detection. This can be helpful because any movement in the needles 10 during detection will obscure their silhouettes, which would render detection less reliable. The magnet assemblies 230 may be electromagnets that can be selectively energized by the machine 200 or permanent magnets. If energized during the operating procedure, assuming the tray 100 is placed within the machine during that procedure, the magnet assemblies 230 may help to retain the needles 10 on the tray 100 during the procedure. Once the needles 10 on the tray 100 have been counted, the magnet assemblies 230 may be de-energized so the tray 100 can be removed from the machine 200 with its needles 10 retained (via either adhesive or a magnetic sheet, or both), and another tray 100 placed in the machine 200 to continue counting additional needles 10. At the conclusion of the operating procedure, once all needles 10 have been counted and accounted for, all of the trays 100 (and their retained needles 10) consumed during the procedure may be discarded.

The machine 200 is configured to include software that is programmed to classify and count the type and number of needles 10 on the tray 100 based on their silhouettes as visualized and detected by the camera 260 (FIG. 8A). Preferably the camera 260 is disposed at a fixed position (focal length) above a station within the machine 200 for receiving trays 100 for needle-counting, so that the relative distance between the camera 260 and a tray 100 in that station is fixed. The machine 200 may include a movable X-Y platform 240 (FIG. 8A) or one or more actuators (not shown) (e.g. linear actuators, motors, solenoids, or pistons) configured to support or engage the tray 100 to move or shift the tray 100 in a direction parallel to the upper surface 102a of the tray 100 (e.g. x-y-direction (see, FIG. 8A)) to improve the accuracy of the machine 200 or if the viewing area of the machine 200 is small compared to the size of the tray 100 (e.g. FIG. 3A illustrates an example viewing area 260a). The movable X-Y platform 240 or the noted actuators (not shown) can adjust a precise X-Y position of the tray 100 during needle detection. A slight movement of the tray 100 in a direction parallel to the upper surface 102a of the tray 100 may aid the machine 200 in recognizing the needle 10 from a slightly different angle. For example, the camera 260 (FIG. 8A), which may be fixed as noted above, can take silhouette images of the needle(s) 10 from more than one perspective where the relationship of the perspectives are known or fixed. Combining image information from multiple perspectives, software can be programmed to execute an algorithm to construct a composite 3D image of the particular needle(s) 10 in order to match them precisely with the number and type known to have been used during surgery—similar to how the human brain constructs 3D images based on combining the perspectives from the left and right eyes. This shift in angle to capture multiple images from different perspectives, or even a single image from a different perspective that better matches that by which a particular needle is recognized, may help the machine 200 improve its recognition of the needle 10.

As noted above, one or more of the receiving areas 105 may include an optical calibration feature 107. The optical calibration feature 107 provides the automated counting and identification machine 200 with a feature of known size and position. Once the machine 200 detects the calibration feature 107 it may use the known size and position of the calibration feature 107 to determine the size and position of the needles 10 on the tray 100. It is contemplated that the lip 106 on the tray 100 can be used as an optical calibration feature. The frequency of the calibration procedure may be programmed into the machine 200, e.g. each time a tray 100 is placed in the machine 200, once per operating procedure, based on time of use, etc.

In summary, as seen in FIG. 8A, the machine 200 includes edge light assemblies 210A-210D that provide light for generating silhouettes of the needles 10 deposited in the respective areas 105 indexed along the upper surface 102a of the tray 100, so that a camera 260 or other optical sensor (not shown) can detect the shape, size and other features of the deposited needle 10 based on its silhouette. In this embodiment, it is desired that the tray 100 is optically transmissive, and it may be preferable that it also is colorless. When illuminated by the edge light assemblies 210A-210D, the tray 100 functions as a collimated backlight, e.g. because the film 112 collimates light transmitted through the tray as described above. The collimated light emanating from the tray 100 (originating from the edge light assemblies 210A-210D) propagates toward an imaging sensor such as a camera 260 located generally above the upper surface 102a of the tray 100. In this manner, the sensor detects an image corresponding to the silhouette of the deposited needle 10.

Referring to FIG. 8A, a processor 600 connected with the camera 260 then can algorithmically classify the gathered data (e.g. using artificial intelligence) or compare the detected silhouette shape against silhouette data corresponding to a plurality of different needles 10 stored in a memory coupled to the processor 600, and thereby identify the particular needle 10 that has been deposited. If the processor 600 is preprogrammed with all needles 10 that are to be used in a particular procedure, or if specific needles 10 are programmed as they are consumed during a procedure, then the processor 600 can be utilized to account for the needles 10 used to help ensure that all such needles 10 are accounted for when the procedure is over. Moreover, the processor 600 can account for the quantities of different categories (e.g. types and styles) of needles 10 based on their unique silhouettes, in order to track the different categories of needles 10 that are used and accounted for at the end of the procedure.

Figure 10:
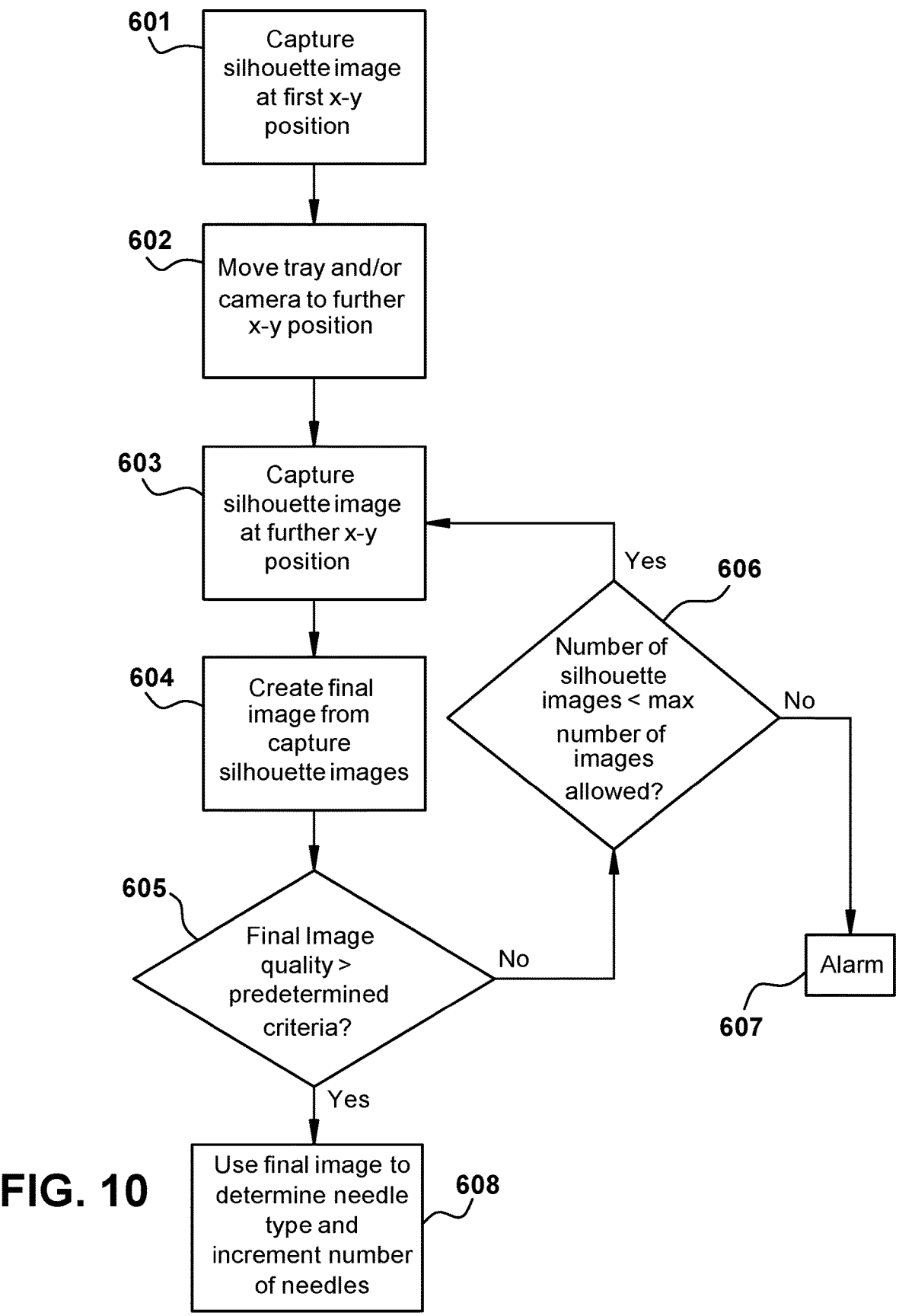
FIG. 10 is a flow chart for a method for identifying and counting needles on a collection and counting tray as disclosed herein.

Referring to FIG. 10, the processor 600 may be programmed to perform the following steps. In Step 601, the camera 260 captures a silhouette image from a first perspective in a first x-y position of the tray 100. In Step 602, the x-y position of the tray 100 and/or the camera 260 is change to a further x-y position. In Step 603, the camera 260 captures a silhouette image from a further perspective in the further x-y position of the tray 100. In Step 604, the processor 600 creates a final image from the captured silhouette images or saves a collection of the capture silhouette images. In Step 605, the processor 600 determines if the final image or the collection of images has a predetermined image quality. If the final image or the collection of images does not achieve the predetermined image quality and the number of capture images is less than a maximum number of images allowed (Step 606), Steps 603-605 are repeated. If after a predetermined maximum number of silhouettes are taken (determined in Step 606) the final image or the collection of images still does not achieve the predetermined image quality, then the processor 600 sounds an alarm for the user (Step 607). If the predetermined image quality is achieved (as determined in step 605), then in Step 608 the processor 600 then can algorithmically classify the gathered data (e.g. using artificial intelligence) or compare the final 3D image against silhouette data corresponding to a plurality of different needles 10 stored in a memory coupled to the processor 600, and thereby identify the particular needle 10 that has been deposited. The foregoing steps are then repeated for each needle 10 on the tray 100 until all the needles 10 are identified and counted.

Referring to FIG. 11, a collection and counting tray 300 according to a second embodiment, for use in an automated counting and identification machine 400 according to the second embodiment (schematically illustrated in FIG. 11) is shown.

Similar to the machine 200 (described in detail above), the machine 400 includes a camera 260 that is positioned above an upper surface 302a of the tray 300 in this embodiment for detecting the needles (not shown) on the tray 300.

In the prior-described embodiment, the tray 100 was edge lit by a lighting assembly that includes edge light assemblies 210A-210D disposed adjacent to respective edges 103 of the tray. In the present embodiment, the tray 300 is an optically transmissive body that is positioned between the camera 260 and a lighting assembly, i.e., a backlight assembly 350. The backlight assembly 350 includes an internally optically reflective body 352 that is itself edge-lit via edge light assemblies 210A-210D similar to those described above for the prior embodiment (only edge light assemblies 210A and 210C are schematically illustrated in FIG. 11 for simplicity.) In this embodiment, the edge light assemblies 210A-210D illuminate the edges of the optically reflective body 352 of the backlight assembly 350, which internally reflects that light and redirects it upward, where it exits through the upper surface of the body 352 and is directed toward the lower surface 306 of the tray 300 opposite where the camera 260 is positioned above the tray. The reflective body 352 can be configured similarly as the tray 100 in the prior-described embodiment, in that it can have a reflective coating at its lower surface and other features designed to redirect reflected light upward and out through its upper surface. That light passes through the optically transmissive tray 300 toward the camera 260, which is thereby able to image silhouettes of needles in the path of that light. The tray 300 can be actuated along an X-Y direction (e.g. using an X-Y platform or actuators as described above) in order to place different receiving areas of the tray 300 in the detection path, and/or to obtain image information from multiple perspectives for a single receiving area.

Similar to the magnet assemblies 230 described in a prior embodiment, the machine 400 in this embodiment may include a magnetic assembly 330 positioned below the backlight assembly 350. The magnetic assembly 330 may be used to retain ferromagnetic needles (not shown) on the tray 300 to ensure they remain fixed in place during silhouette visualization and detection when aligned along the detection path—i.e. the path of light between the backlight assembly 350 and the camera 260. The magnet assemblies 330 may be electro-magnets that can be selectively energized by the machine 400 or permanent magnets.

It is contemplated that a filter 370 may be positioned between the camera 260 and the tray 300. The filter 370 may be configured to allow light of only the predetermined wavelength to pass from the tray 300 to the camera 260.

Figure 12A:
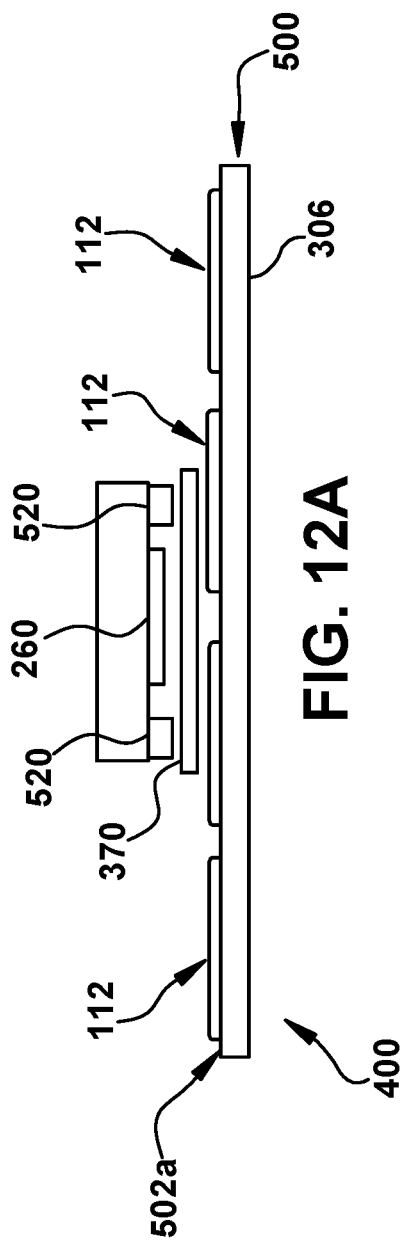
FIG. 12A is a side schematic view of a collection and counting tray according to a third embodiment positioned in an automated counting and identification machine according to the third embodiment.
Figure 12B:
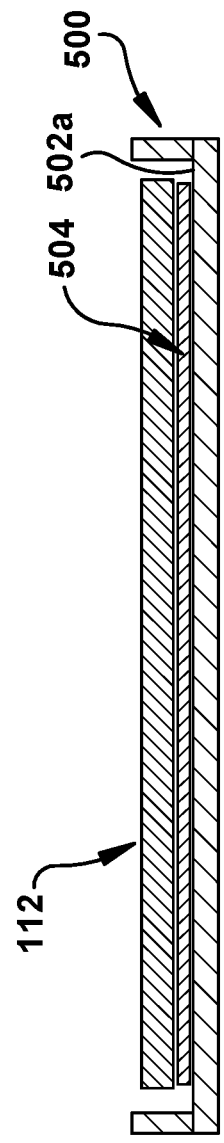
FIG. 12B is a cross-sectional view of the collection and counting tray of FIG. 12A.

Referring to FIGS. 12A and 12B, a tray 500 (and associated counting and identification machine) according to another embodiment is illustrated. Unlike the trays 100, 300 previously discussed, the tray 500 is configured to be used in conjunction with one or more light sources 520 that illuminates an upper surface 502a of the tray 500. Similar to one embodiment describe above, the tray 500 can include graphics (not shown) that are human readable but transmissive to the light of a predetermined wavelength. An absorbing element 504 (FIG. 12B) is positioned on or applied to the upper surface 502a. The absorbing element 504 is made from a material that is configured to absorb light of the predetermined wavelength. The predetermined wavelength is selected to be a light wavelength that is reflected by the needles (not shown) on the tray 500.

During use, the light of the predetermined wavelength is directed onto the upper surface 502a of the tray 500 from light sources 520, and only the light reflected by the needles (not shown) is sent back to the camera 260 positioned above the upper surface 502a of the tray 500. As described in detail above, the camera 260 may be configured to detect the light reflected by the needles and to use the reflected light to determine and count the needles on the tray 500, in a similar manner as described in detail above. In this embodiment, the camera 260 and light sources 520 can be provided in or as part of a common overhead assembly that can be moved along an X-Y direction parallel to the upper surface 502a of the tray 500—similar to as described above for the camera in earlier embodiments. In this manner, the camera 260 can interrogate different receiving areas on the tray 500, or the same receiving area from different perspectives in order to obtain 3-dimensional information concerning a particular surgical implement in that receiving area. Alternatively, the tray 500 itself may be disposed on an X-Y table or otherwise be movable in the X-Y plane using actuators.

When compared to manual needle handling and counting, the embodiments disclosed herein enable an integrated and automated approach to handling, identification, counting, needle disposal and manual audits.

Although the aforementioned embodiments have been described with respect to surgical needles, it will be appreciated that those embodiments also may be utilized to account for and keep track of other surgical tools and instrumentalities used during any surgical procedure, such as surgical sponges or other conventional surgical instrumentalities, whose respective silhouettes also can be programmed into a processor and detected by a camera or other sensor for comparison to stored silhouette parameters.

The systems for tracking and accounting for surgical needles or other surgical instrumentalities as disclosed herein can be incorporated in or utilized with or as part of other systems for monitoring surgical objects during surgery; for example that disclosed in US Patent Application Publication No. 2019/0362839, the contents of which are incorporated herein by reference. For example, the system disclosed herein can feed data to the monitoring system disclosed therein, which then can tabulate the needles or other instruments that have been accounted for using the instant embodiments, and if desired, display the counts on the display screen 108, also disclosed therein.

What is claimed:

1. A surgical implement collecting tray comprising:
   an optically transmissive body having a lower surface, an upper surface, and one or more edges disposed about a periphery of the optically transmissive body, at least one of the lower surface or the one or more edges configured to receive light from an adjacent light source, wherein the optically transmissive body is configured to transmit at least a portion of the received light through the upper surface;
   a plurality of defined receiving areas on the upper surface and configured to receive respective surgical implements therein, said receiving areas being defined by prismatic embossments that protrude from the upper surface of said optically transmissive body and are configured to redirect light incident thereon back into said optically transmissive body,
   wherein the surgical implement collecting tray is configured to direct light away from the upper surface.

2. The surgical implement collecting tray of claim 1, further comprising a collimating film disposed on the upper surface of said optically transmissive body effective to direct the light exiting said upper surface in a collimated direction.

3. The surgical implement collecting tray of claim 1, further comprising:
   a reflective layer at the lower surface of said optically transmissive body adapted to redirect light incident thereon toward the upper surface.

4. The surgical implement collecting tray of claim 1, further comprising:
   a reflective layer at said one or more edges for directing light incident thereon into the optically transmissive body.

5. The surgical implement collecting tray of claim 2, comprising an optically transmissive adhesive applied adjacent to the upper surface of said collimating film.

6. The surgical implement collecting tray of claim 1, further comprising:
   a lip disposed about a periphery of the upper surface of said optically transmissive body for re-directing light toward said optically transmissive body.

7. The surgical implement collecting tray of claim 1, said embossments defining gridlines formed in the upper surface of said optically transmissive body.

8. The surgical implement collecting tray of claim 1, said receiving areas being defined by graphics printed on the upper surface of the optically transmissive body that are transmissive to light in a predetermined range of wavelengths.

9. The surgical implement collecting tray of claim 3, comprising a magnet positioned beneath said lower surface of the optically transmissive body, wherein the magnet is a magnetic sheet attached to the reflective layer.

10. The surgical implement collecting tray of claim 1, further comprising a surgical implement deposited into at least one said receiving area of the surgical implement collecting tray.

11. The surgical implement collecting tray of claim 10, said surgical implement comprising a needle.

12. A surgical-implement counting system, comprising:
    the surgical implement collecting tray of claim 1; and
    an edge light assembly configured to illuminate an adjacent one of the one or more edges of the optically transmissive body of said surgical implement collection tray.

13. The surgical-implement counting system of claim 12, the edge light assembly comprising:
    a plurality of light collecting lenses associated or configured to be aligned with respective light emitting diodes, said light collecting lenses all being coupled to a light pipe that extends along an adjacent edge of said optically transmissive body and is configured to receive light emitted by the light emitting diodes; and an exit diffuser also extending along the adjacent edge of said optically transmissive body and configured to direct light from the light pipe to said adjacent edge of said optically transmissive body.

14. A system for identifying and counting surgical implements, the system comprising:
a counting machine comprising:
a station configured to receive therein a surgical implement collecting tray having surgical implements disposed thereon, the surgical implement collecting tray comprising:
an optically transmissive body having a lower surface, an upper surface, and one or more edges disposed about a periphery of the optically transmissive body, at least one of the lower surface or the one or more edges configured to receive light from an adjacent light source, wherein the optically transmissive body is configured to transmit at least a portion of the received light through the upper surface;
a plurality of defined receiving areas on the upper surface and configured to receive respective surgical implements therein,
wherein the surgical implement collecting tray is configured to direct light away from the upper surface, and;
a lighting assembly adapted to direct light toward the surgical implement collecting tray when received in said station, said light assembly comprising:
a light collecting lens associated or configured to be aligned with a light emitting diode, said light collecting lens being coupled to a light pipe that extends along an adjacent edge of said surgical implement collecting tray when received in said station, said light pipe being configured to receive light emitted by the light emitting diode; and
an exit diffuser also extending along the adjacent edge of said surgical implement collecting tray when received in said station and configured to direct light from the light pipe to said edge of said surgical implement collecting tray when received in said station.

15. The system of claim 14, further comprising a processor being adapted to count a plurality of the thusly recognized particular surgical implements during or appurtenant to an operating procedure.

16. A system for identifying and counting surgical implements, the system comprising:
a counting machine comprising:
a station configured to receive therein a surgical implement collecting tray having surgical implements disposed thereon, the surgical implement collecting tray comprising:
an optically transmissive body having a lower surface, an upper surface, and one or more edges disposed about a periphery of the optically transmissive body, at least one of the lower surface or the one or more edges configured to receive light from an adjacent light source, wherein the optically transmissive body is configured to transmit at least a portion of the received light through the upper surface; and
a plurality of defined receiving areas on the upper surface and configured to receive respective surgical implements therein,
wherein the surgical implement collecting tray is configured to direct light away from the upper surface, and
a lighting assembly adapted to direct light toward the surgical implement collecting tray when received in said station, said lighting assembly comprises:
a backlight assembly disposed beneath the station for receiving said surgical implement collecting tray and configured to direct light upward through said station and into and through a lower surface of said surgical implement collecting tray, the backlight assembly comprising a light collecting lens aligned with a light emitting diode, said light collecting lens being coupled to a light pipe that extends along an adjacent edge of an internally optically reflective body, said internally optically reflective body being configured to direct light received from said light pipe toward the lower surface of said surgical implement collecting tray when said surgical implement collecting tray is received in said station.

17. The system of claim 14, further comprising:
an actuator adapted to move the surgical implement collecting tray when received in said station in a plane parallel to an upper surface of the surgical implement collecting tray.

18. The system of claim 14, further comprising:
an actuator adapted to move the sensor in a plane parallel to an upper surface of the surgical implement collecting tray.

19. The system of claim 14, said lighting assembly disposed above said station and adapted to illuminate an upper surface of said surgical implement collecting tray when received in said station.

20. The system of claim 19, further comprising said surgical implement collecting tray received in said station, and an absorbing element positioned on or applied to said upper surface of said surgical implement collecting tray, said absorbing element adapted to absorb said light from said lighting assembly.

21. A surgical implement collecting device comprising:
an optically transmissive body having a lower surface, an upper surface, and one or more edges disposed on opposite sides of the optically transmissive body, at least one of the lower surface or the one or more edges configured to receive light from an adjacent light source, wherein the optically transmissive body is configured to transmit at least a portion of the received light through the upper surface;
a plurality of defined receiving areas on the upper surface and configured to receive respective surgical implements therein, said receiving areas being defined by prismatic embossments that protrude from the upper surface of said optically transmissive body and are configured to redirect light incident thereon back into said optically transmissive body,
wherein the collecting device is configured to direct light away from the upper surface.

22. The surgical implement collecting device of claim 21, further comprising a collimating film disposed on the upper surface of said optically transmissive body effective to direct the light exiting said upper surface in a collimated direction.

23. The surgical implement collecting device of claim 21, further comprising:
a reflective layer at the lower surface of said optically transmissive body adapted to redirect light incident thereon toward the upper surface.

24. The surgical implement collecting device of claim 21, further comprising:
- a reflective layer at said one or more edges for directing light incident thereon into the optically transmissive body.

25. The surgical implement collecting device of claim 21, said embossments defining gridlines in the upper surface of said optically transmissive body.

26. The surgical implement collecting device of claim 21, said receiving areas being defined by graphics printed on the upper surface of the optically transmissive body that are transmissive to light in a predetermined range of wavelengths.

27. The surgical implement collecting device of claim 23,
- wherein a magnet is a magnetic sheet attached to the reflective layer.

28. The surgical implement collecting tray of claim 1, further comprising:
- at least one of:
  - an optically transmissive adhesive, above the upper surface of said optically transmissive body, onto which a surgical implement may be placed and securely held within one receiving area, or
  - a magnet positioned beneath the lower surface of said optically transmissive body and adapted to attract ferromagnetic surgical implements disposed in the receiving areas of the surgical implement collecting tray via magnetic interaction therewith through said optically transmissive body.

29. The system of claim 14, further comprising:
- at least one of:
  - an optically transmissive adhesive, above the upper surface of said optically transmissive body, onto which a surgical implement may be placed and securely held within one receiving area, or
  - a magnet positioned beneath the lower surface of said optically transmissive body and adapted to attract ferromagnetic surgical implements disposed in the receiving areas of the surgical implement collecting tray via magnetic interaction therewith through said optically transmissive body.

30. The system of claim 14, further comprising:
- a sensor mounted above said station and adapted to detect silhouetted images of surgical implements disposed on said surgical implement collecting tray when received in said station from the light directed thereto from the said lighting assembly; and
- a processor adapted to determine a size and number of said surgical implements from said silhouetted images, thereby recognizing particular surgical implements.

* * * * *